US006231519B1

(12) United States Patent
Blants et al.

(10) Patent No.: US 6,231,519 B1
(45) Date of Patent: May 15, 2001

(54) METHOD AND APPARATUS FOR PROVIDING AIR QUALITY ANALYSIS BASED ON HUMAN REACTIONS AND CLUSTERING METHODS

(75) Inventors: Lioudmila Blants; Pekka Heinonen, both of Espoo; Mikko Makipaa; Harri Wikberg, both of Helsinki, all of (FI)

(73) Assignee: Nokia Corporation, Espoo (FI)

( * ) Notice: Subject to any disclaimer, the term of this patent is extended or adjusted under 35 U.S.C. 154(b) by 0 days.

(21) Appl. No.: 09/304,348

(22) Filed: May 4, 1999

(51) Int. Cl.[7] ...................................................... A61B 5/08
(52) U.S. Cl. ........................... 600/529; 600/300; 128/904
(58) Field of Search ................................. 600/300–301, 600/529–538; 128/903–904, 920–925; 706/930; 434/130; 422/900; 455/12.1–13.4

(56) References Cited

U.S. PATENT DOCUMENTS

| 5,827,180 | * | 10/1998 | Goodman | 600/300 |
| 5,831,876 | * | 11/1998 | Orr et al. | 706/930 |
| 5,836,312 |   | 11/1998 | Moore . | |
| 5,892,690 |   | 4/1999  | Boatman et al. . | |

FOREIGN PATENT DOCUMENTS

| 0 527 307 A2 | 2/1993  | (EP) . |
| WO 91/03979  | 4/1991  | (WO) . |
| WO 95/32480  | 11/1995 | (WO) . |

OTHER PUBLICATIONS

G. Cirrincione et al., *A Neural Network Architecture for Static Security Mapping in Power Systems*, pp. 1611–1614, IEEE, 1996.

* cited by examiner

*Primary Examiner*—Cary O'Connor
*Assistant Examiner*—Michael Astorino
(74) *Attorney, Agent, or Firm*—Altera Law Group, LLC

(57) ABSTRACT

A method and apparatus to collect risk factor information and location data associated with asthma patients and to provide information to these patients about the air quality is disclosed. A mobile two-way communication tool is used to facilitate air quality analysis based on human reactions and clustering methods. The method includes measuring predetermined physiological and dynamic parameters associated with a user, transmitting the measured predetermined parameters to an analysis tool, analyzing the measured physiological and dynamic predetermined parameters to determine advisory information associated with the measured predetermined physiological and dynamic parameters and transmitting the advisory information to the user. The measuring predetermined physiological and dynamic parameters associated with a user includes measuring physiological conditions of the user, such as respiratory function indications. The dynamic parameters includes local information such as the time of day and/or geographic locations. The transmitting is performed using a mobile phone, a mobile 2-way pager, a wireless personal digital assistant or an Internet accessing device, and the analyzing includes mapping the data using a self-organizing map.

34 Claims, 2 Drawing Sheets

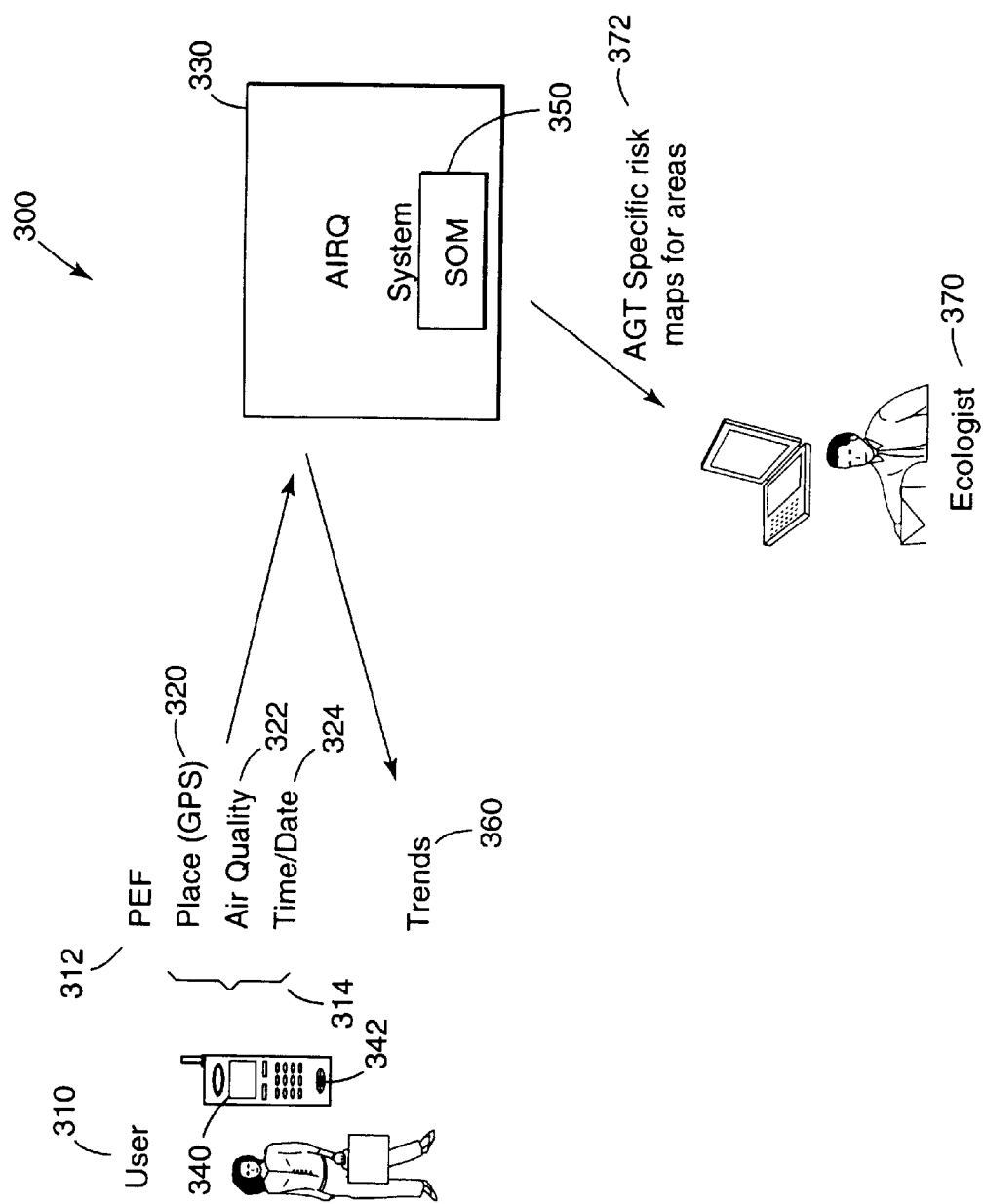

METHOD AND APPARATUS FOR PROVIDING AIR QUALITY ANALYSIS BASED ON HUMAN REACTIONS AND CLUSTERING METHODS

BACKGROUND OF THE INVENTION

1. Field of the Invention

This invention relates in general to telecommunications, and more particularly to a method and apparatus for using a mobile communication tool to provide air quality analysis based on human reactions and clustering methods.

2. Description of Related Art

Both the prevalence of patients suffering from respiratory diseases, such as pulmonary emphysema, asthma, chronic obstructive pulmonary disease (COPD) and bronchitis, and the cost of treating those patients is rising dramatically. For example, about 15 million people in the United States have asthma with more than 100 million days of restricted activity annually. In May 1998, the Department of Health and Human Services in the United States estimated that healthcare costs for asthma was more than $6 billion a year. Further, in January 1997, the National Institute of Allergy and Infectious Diseases estimated that the loss in productivity by working parents caring for children who miss school due to asthma: was $1 billion a year. In addition, the incidence of asthma has increased dramatically, e.g., in Finland the number of children taking medication for asthma in 1986 was 6,400, but increased to 21,600 by 1996. Therefore, new research in controlling respiratory diseases such as asthma continues to find widespread public and private support.

Asthma is a chronic inflammatory disorder of the airways. In susceptible individuals this inflammation causes recurrent episodes of coughing, wheezing, chest tightness, and difficult breathing. Inflammation makes the airways sensitive to stimuli such as allergens, chemical irritants, tobacco smoke, cold air, or exercise. When exposed to these stimuli, the airways may become swollen, constricted, filled with mucus, and hyper-responsive to stimuli. The resulting airflow limitation is reversible (but not completely so in some patients), either spontaneously or with treatment. When asthma therapy is adequate, inflammation can be reduced over the long term, symptoms can usually be controlled, and most asthma-related problems prevented.

As suggested above, preventing the development of asthma attacks is a major goal of current research. Evidence now indicates that the strongest risk factors for developing asthma are exposure to environmental factors, such as allergens irritants. The identification and control of triggers, i.e., factors that precipitate symptoms and attacks of asthma, are essential for successful asthma management. For example, at least the following factors have been identified as triggers: tobacco smoke (active and passive), air pollution and smoke in cities, cockroach allergens, dust mites, cat and other pet allergens, pollen, mold spores, low atmosphere ozone, low or high air temperature, low or high air humidity and ambient chemicals and gases.

In addition to the separate risk factors, each individual reacts differently to each of these, and to different combinations of these risk factors. When common allergens and irritants that trigger attacks are removed from the patient's environment, asthma symptoms and hospitalizations can be prevented and medications reduced.

Avoiding triggers means changing behavior, which may be very difficult for some patients or families. Each asthma patient must work to find the most appropriate ways to avoid his or her triggers. Some television networks already provide basic information about pollens (birch tree, hay, etc.) and basic information about ozone levels is available in some locations. However, this information is in very general form, and an individual does not have the means to estimate the overall effects from a subjective point of view. Further, objective measurements are important because patients and physicians often do not recognize asthma symptoms or their severity. Thus, lung function measurements are used to assess airflow limitation and help diagnose and monitor the course of asthma. Accordingly, lung function measurements for asthma management are used in the same manner as blood pressure measurements for diagnosing and monitoring hypertension.

Peak flow meters measure peak expiratory flow (PEF), the fastest rate at which air moves through the airways during a forced expiration. PEF provides a simple, quantitative, reproducible measure of airway obstruction. Peak flow meters are cheap, lightweight and portable. Further, repeated measures are usually highly reproducible with each individual patient.

Nevertheless, the ability of individuals to identify what combinations of risk factors, e.g., location, allergen and irritant, increase the likelihood of an attack is very difficult, if not impossible. However, it would be extremely valuable for each individual with asthma to better identify these situations to better manage their disease and symptoms. In principle, it would be possible to give information about the air quality to each individual, but in practice this is impossible since all the needed measurement devices for all possible risk factors, and in all needed locations are not available.

It can also be seen that there is a need for a method and apparatus to collect risk factor information and location data associated with asthma patients and to provide information to these patients about the air quality.

It can also be seen that there is a need for a system that uses a mobile two-way communication tool to facilitate air quality analysis based on human reactions and clustering methods.

SUMMARY OF THE INVENTION

To overcome the limitations in the prior art described above, and to overcome other limitations that will become apparent upon reading and understanding the present specification, the present invention discloses a method and apparatus to collect risk factor information and location data associated with asthma patients and to provide information to these patients about the air quality.

The present invention solves the above-described problems by providing a system that uses a mobile two-way communication tool to facilitate air quality analysis based on human reactions and clustering methods.

A method in accordance with the principles of the present invention includes measuring predetermined physiological and dynamic parameters associated with a user, transmitting the measured predetermined parameters to an analysis tool, analyzing the measured physiological and dynamic predetermined parameters to determine advisory information associated with the measured predetermined physiological and dynamic parameters and transmitting the advisory information to the user.

Other embodiments of a method in accordance with the principles of the invention may include alternative or optional additional aspects. One such aspect of the present invention is that the measuring predetermined physiological and dynamic parameters associated with a user includes measuring physiological conditions of the user.

Another aspect of the present invention is that the physiological conditions includes respiratory function indications.

Another aspect of the present invention is that the dynamic parameters includes local information.

Another aspect of the present invention is that the local information includes a time of day.

Another aspect of the present invention is that the local information includes geographic locations.

Another aspect of the present invention is that the transmitting is performed using a mobile phone, a mobile 2-way pager, a wireless personal digital assistant or an Internet accessing device.

Another aspect of the present invention is that the analyzing includes mapping the data using a self-organizing map.

Another aspect of the present invention is that the advisory information includes a risk map.

Another aspect of the present invention is that the risk map includes a warning associated with a location of a user, wherein the location is identified as having a high risk associated therewith.

Another aspect of the present invention is that the risk is personal to the user.

Another aspect of the present invention is that the risk is associated with an asthma type.

These and various other advantages and features of novelty which characterize the invention are pointed out with particularity in the claims annexed hereto and form a part hereof. However, for a better understanding of the invention, its advantages, and the objects obtained by its use, reference should be made to the drawings which form a further part hereof, and to accompanying descriptive matter, in which there are illustrated and described specific examples of an apparatus in accordance with the invention.

BRIEF DESCRIPTION OF THE DRAWINGS

Referring now to the drawings in which like reference numbers represent corresponding parts throughout:

FIG. 3 illustrates a system level diagram of the process illustrated in FIG. 2.

DETAILED DESCRIPTION OF THE INVENTION

In the following description of the exemplary embodiment, reference is made to the accompanying drawings which form a part hereof, and in which is shown by way of illustration the specific embodiment in which the invention may be practiced. It is to be understood that other embodiments may be utilized as structural changes may be made without departing from the scope of the present invention.

The present invention provides a method and apparatus to collect risk factor information and location data associated with asthma patients and to provide information associated with the air quality to these patients. A mobile communication tool is used to provide air quality analysis based on human reactions and clustering methods. The present invention creates automatically relevant clusters of all individuals with asthma and information is personalized by the cluster type and by physical location. The present invention is also adaptive and, therefore, it will learn new risk factors all the time and also their interaction.

Figure 1:
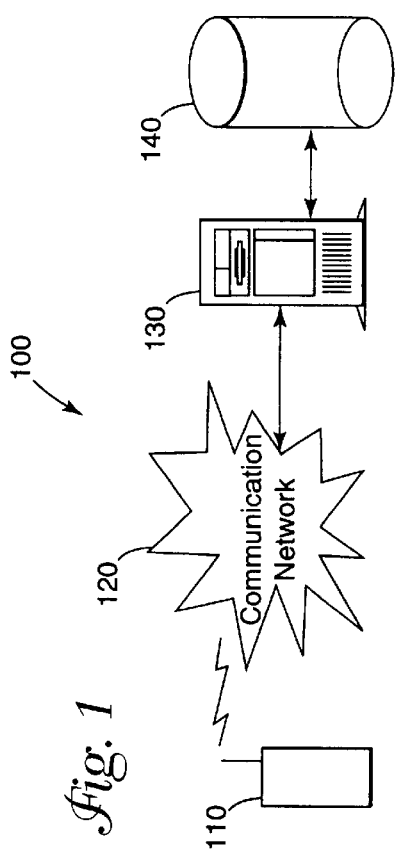
FIG. 1 illustrates a system for providing air quality analysis based on human reactions and clustering methods according to the present invention.

FIG. 1 illustrates a system 100 for providing air quality analysis based on human reactions and clustering methods according to the present invention. In FIG. 1, a two way mobile data communication tool 110, such as a mobile phone, a mobile 2-way pager, a wireless personal digital assistant or an wireless Internet accessing device, is used to provide physiological measurements, such as respiratory function indications using a Peak Expiratory Flow meter, to a server using the communication network 120. The mobile communication tool also provides dynamic parameters, such as a location parameter according to user input, a location service process, i.e., global positioning system, timing advance positioning mechanisms, time of arrival positioning mechanism, enhanced observed time difference position mechanism, other positioning techniques which may be performed by a mobile communications network, or a combination thereof Accordingly, a large collection of data may be assembled in a database when many individuals with asthma collect data using, for example, a simple PEF meter and a two way mobile data communication tool, e.g., mobile communication tool with short messaging service (SMS) capability or a two way pager, and capabilities for enabling position identification, which may be performed by the mobile communication tool and/or the mobile communications network.

The data from the mobile communication tool is provided to a server 130, which uses a multidimensional data clustering method to identify the different asthma types and connect the symptoms of each type with different types of air quality patterns. This data may be assembled so as to be representative of any predetermined area, e.g. a local service area, a regional area, a national area, etc.

Figure 2:
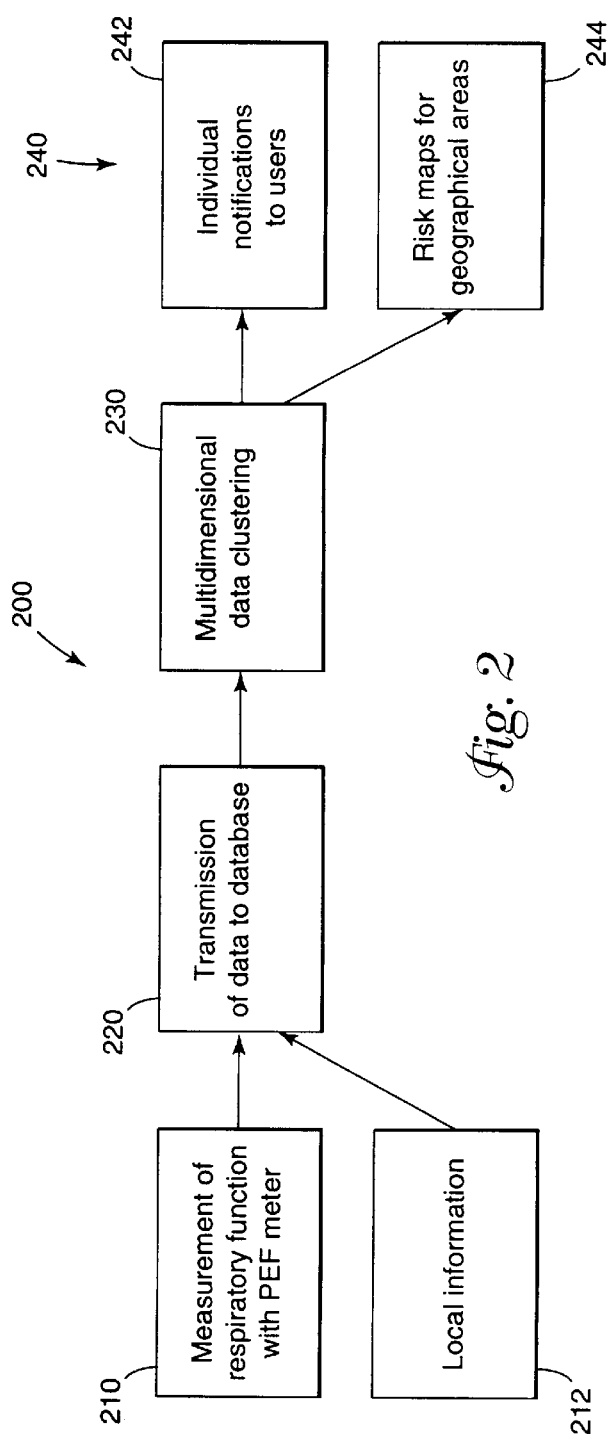
FIG. 2 illustrates the flow chart for the method for providing air quality analysis based on human reactions and clustering methods.

FIG. 2 illustrates the flow chart 200 for the method for providing air quality analysis based on human reactions and clustering methods. In FIG. 2, a user measures their respiratory functions with a peak expiration flow (PEF) meter 210. Local information, such as geographic location, is also obtained 212. Many individuals make these measurements and the PEF data and the local information is transmitted to the database 220. Each data set is combined with the data of all other individuals. In addition, the local ambient information, e.g., temperature, ozone, humidity, pollens, pollution, dust in air, etc. from national meteorology institute and air property measurement stations is combined with the data. All the data is analyzed using multidimensional data clustering 230. The analysis allows cross-correlation and cross-mapping of the data. From this data, advisory information is given to individuals 240. Such feedback may be in the form of individual notification to users 242 and/or risk maps for geographical areas 244 may be provided to the users.

FIG. 3 illustrates a system level diagram 300 of the process illustrated in FIG. 2. In FIG. 3, individuals with asthma (user) 310 follow their symptoms, medication, and pulmonary functions 312 during the day and provide that information along with dynamic location 314 information such as location 320 air quality 322 and time/date 324 to the air quality (AIRQ) database 330 for analysis. The individuals may provide estimates of their individual asthma related air quality when the individual is in an area where there are no other air quality measurement devices. Further, the time/date information 324 may be used to predict and identify seasonal effects such as mold and pollen.

An asthma related menu 340 on a two-way mobile communication tool 342, e.g., mobile communication tool, the mobile communication tool is used to provide data about location, medication, symptoms, etc. The individual then transmits to the air quality (AIRQ) database, for example, as all the collected data to a database as an SMS message.

Using the modem multidimensional data clustering, e.g., in the form of self-organizing maps (SOM) 350, the different asthma types are recognized and the symptoms of each type are connected with different types of air quality patterns. In the learning phase, the SOM 350 forms the Asthma Cluster Types (ACT) and correlates their symptoms with various air quality situations.

It is appreciated that the analysis tools described herein are known by those skilled in the art. For example, self-organizing mapping is one well-known technique as described in "Self-Organizing Maps", (2nd Edition) by Kohonen, Teuvo, Springer Series in Information Sciences, (1997), which is herein incorporated by reference. Further, those skilled in the art will recognize that the present invention is not meant to be limited to a particular type of analysis tool, but that other analysis tools could be used in accordance with the teachings of the present invention.

The results or trends 360 are available back to each individual 310 as private advice and also to the general public as general air quality maps. Thus, individuals will get a warning if they go to an area where the risk level is high for their particular ACT. The data may be used to create ACT specific risk maps for cities and also for larger or smaller areas.

In addition to the physical measurement information, the symptom information coming from individuals with asthma, may automatically reveal some specific risk locations in the environment, e.g. some public building may grow moldy and the most sensitive asthmatics may react to it, but they are not yet willing to make an official complaint about it. However, if many individuals independently indicate that in some specific building they get symptoms, the environmental officials 370 may go and check the reason for the common symptoms, e.g., factory emissions, etc.

Thus, ACT specific risk maps 372 are available to these environmental officials 370. While one individual with asthma is not able to collect all the needed data, even one percent of all asthmatic people would easily provide thousands or tens of thousands measurements per day. This would be enough to create Asthma Cluster Type (ACT) specific risk maps 372. In addition, each individual 310 would also know their own ACT so that they could search the air quality (AIRQ) database 330. For example, an individual could search the database 330 for high risk locations so that the most risky locations could be avoided or the needed medication could be taken at the right time before the serious symptoms flare up.

The individuals 310 with asthma would thus form a living network of measurement "devices" who provide the basic data for clustering, and the analyzed data is provided back to everybody in easy forms, e.g. as ACT specific risk maps, e.g., via TV or Internet.

The foregoing description of the exemplary embodiment of the invention has been presented for the purposes of illustration and description. It is not intended to be exhaustive or to limit the invention to the precise form disclosed. Many modifications and variations are possible in light of the above teaching. It is intended that the scope of the invention be limited not with this detailed description, but rather by the claims appended hereto.

What is claimed is:

1. A method for providing advisory information to a user on environmental factors affecting the user's health; comprising:

measuring from the user environmental factors based upon predetermined physiological and dynamic parameters associated with a user;

transmitting the measured predetermined parameters to an analysis tool;

analyzing the measured physiological and dynamic predetermined parameters to determine advisory information on environmental factors affecting the user's health and associated with the measured predetermined physiological and dynamic parameters; and providing the advisory information to the user.

2. The method of claim 1 wherein the measuring predetermined physiological and dynamic parameters associated with a user comprises measuring physiological conditions of the user.

3. The method of claim 2 wherein the physiological conditions comprises respiratory function indications.

4. The method of claim 2 wherein the dynamic parameters comprises local information.

5. The method of claim 4 wherein the local information comprises a time of day.

6. The method of claim 4 wherein the local information comprises a date.

7. The method of claim 6 wherein the date is used to determine seasonal effects.

8. The method of claim 4 wherein the local information comprises geographic locations.

9. The method of claim 1 wherein the providing comprises transmitting the advisory information to the user using a mobile phone, a mobile 2-way pager, a wireless personal digital assistant or an Internet accessing device.

10. The method of claim 1 wherein the providing comprises enabling a user to perform a search for the advisory information.

11. The method of claim 1 wherein the analyzing includes mapping the measured predetermined parameters.

12. The method of claim 11 wherein the mapping further comprises processing the measured predetermined parameters using a self-organizing map.

13. The method of claim 1 wherein the analyzing includes cross-correlating and cross-mapping the measured predetermined parameters.

14. The method of claim 1 wherein the advisory information comprises a risk map.

15. The method of claim 14 wherein the risk map comprises a warning associated with a location of a user, wherein the location is identified as having a high risk associated therewith.

16. The method of claim 15 wherein the risk is personal to the user.

17. The method of claim 15 wherein the risk is associated with an asthma type.

18. A system for providing air quality analysis to a user of a mobile communication tool, comprising:

means for measuring from the user predetermined physiological and dynamic parameters associated with a user;

a two way mobile data communication tool for transmitting physiological and dynamic parameters associated with the user using a communication network;

a server, coupled to the communication network, for receiving the physiological and dynamic parameters and developing a database for providing feedback including advisory information to the user on the air quality based on the predetermined physiological and dynamic parameters associated with the user measured from the user.

19. The system of claim 18 wherein the physiological parameters of the user comprise physiological conditions of the user.

20. The system of claim 19 wherein the physiological conditions of the user comprise respiratory function indications.

21. The system of claim 18 wherein the dynamic parameters comprise local information.

22. The system of claim 21 wherein the local information comprises a time of day.

23. The system of claim 21 wherein the local information comprises a date.

24. The system of claim 23 wherein the date is used to determine seasonal effects.

25. The system of claim 21 wherein the local information comprises geographic locations.

26. The system of claim 18 wherein the a two way mobile data communication tool comprises a mobile phone, a mobile 2-way pager, a wireless personal digital assistant or an Internet accessing device.

27. The system of claim 18 wherein the server enables a user to perform a search for the advisory information.

28. The system of claim 18 wherein the server maps the measured predetermined parameters.

29. The system of claim 28 wherein the server maps the measured predetermined parameters using a self-organizing map.

30. The system of claim 18 wherein the server cross-correlates and cross-maps the measured predetermined parameters.

31. The system of claim 18 wherein the advisory information comprises a risk map.

32. The system of claim 31 wherein the risk map comprises a warning associated with a location of a user, wherein the location is identified as having a high risk associated therewith.

33. The system of claim 32 wherein the risk is personal to the user.

34. The method of claim 32 wherein the risk is associated with an asthma type.

* * * * *